US012708695B2

(12) United States Patent
Procter et al.

(10) Patent No.: US 12,708,695 B2
(45) Date of Patent: Aug. 18, 2026

(54) SOFT TISSUE ADHESIVE COMPOSITION OF ALPHA-TCP AND PHOSPHORYLATED AMINO ACID

(71) Applicant: BIOMIMETIC INNOVATIONS LIMITED, Shannon (IE)

(72) Inventors: Philip Procter, Divonne les Bains (FR); Håkan Engqvist, Uppsala (SE); Michael Pujari-Palmer, Uppsala (SE); Gerard Insley, Limerick (IE)

(73) Assignee: BIOMIMETIC INNOVATIONS LIMITED, Shannon (IE)

( * ) Notice: Subject to any disclaimer, the term of this patent is extended or adjusted under 35 U.S.C. 154(b) by 322 days.

(21) Appl. No.: 18/612,434

(22) Filed: Mar. 21, 2024

(65) Prior Publication Data

US 2024/0226370 A1 Jul. 11, 2024

Related U.S. Application Data

(63) Continuation of application No. 16/337,350, filed as application No. PCT/EP2017/074553 on Sep. 27, 2017, now Pat. No. 11,964,072.

(30) Foreign Application Priority Data

Sep. 27, 2016 (SE) .................................. 1651271-7
Dec. 22, 2016 (SE) .................................. 1651727-8

(51) Int. Cl.
*A61L 24/00* (2006.01)
*A61L 24/02* (2006.01)
*A61L 27/54* (2006.01)

(52) U.S. Cl.
CPC ....... *A61L 24/0031* (2013.01); *A61L 24/0084* (2013.01); *A61L 24/02* (2013.01); *A61L 27/54* (2013.01); *A61L 2430/34* (2013.01)

(58) Field of Classification Search
CPC .. A61L 24/0031; A61L 24/02; A61L 2400/06; A61L 2430/34; A61L 24/0084; A61L 27/54; A61L 24/001
See application file for complete search history.

(56) References Cited

U.S. PATENT DOCUMENTS 6,533,821 B1 3/2003 Lally
8,105,086 B2 1/2012 Asgary
11,247,941 B2 2/2022 Hess et al.
11,638,777 B2 5/2023 Hess et al.
2005/0217538 A1 10/2005 Reinstorf et al.
2009/0087390 A1 4/2009 Modi
2010/0121459 A1 5/2010 Garigapati et al.
2011/0277931 A1 11/2011 Garigapati et al.
2012/0288446 A1 11/2012 Garigapati et al.
2013/0122057 A1 5/2013 Garigapati et al.
2020/0030483 A1 1/2020 Procter
2020/0038545 A1 2/2020 Procter

FOREIGN PATENT DOCUMENTS

CN 101014376 A 8/2007
WO WO 2006/041365 4/2006
WO WO 2016/196371 12/2016
WO WO 2018/060287 4/2018

OTHER PUBLICATIONS

Coppey E, et al;. "Early Complications From the Use of Calcium Phosphate Paste in Mandibular Lengthening Surgery. A Retrospective Study" J Oral Maxillofac Surg. 2017;75(6):1274.e1-1274.e10. doi:10.1016/j.joms.2017.01.017.
Correa et al., "α-Tricalcium phosphate cements modified with β-dicalcium silicate and tricalcium aluminate: Physicochemical characterization, in vitro bioactivity and cytotoxicity", J. Biomedical Materials Research B: Applied Biomaterials, Jan. 2015, vol. 103B, Issue 1:72-83.
Dorozhkin, "Calcium orthophosphate-based biocomposites and hybrid biomaterials", J Mater Sci (2009) 44:2343-2387.
Duan, et al., "Applications of Bioadhesives: A Mini Review", Frontiers in Bioengineering and Biotechnology, Sep. 2021 vol. 9:7; 1-12.
Ge, et al., "Review: Recent Advances in Tissue Adhesives for Clinical Medicine", Polymers, (2020) 12:939 p. 1-22.
HexArmor, "Concrete irritation, Burns, and dermatitis", Retrieved Aug. 26, 2022, from https://www.hexarmor.com/posts/concrete-irritation-burns-and-dermatitis.
International Search report for PCT/EP2017/074551, dated Dec. 13, 2017, 3 pages.
International Search report for PCT/EP2017/074553, dated Dec. 13, 2017, 3 pages.
Li, et al., "Ability of Obturation Materials to Improve the Seal of the Root Canal System—a Review", Acta Biomater. (2014) 10(3): pp. 1050-1063.
Morejon-Alonso et al., "Effects of Silica Addition on the Chemical, Mechanical and Biological Properties of a New α-Tricalcium Phosphate/Tricalcium Silicate Cement", Materials Research, 2011, 14(4): 475-482.
Mostafa et al., "Injectable Bone Cement Based on Calcium Silicate and Calcium Phosphate", Int. J. Chem. Sci.: 13(1), 2015: 80-96.
Motisuke et al., "Apatite bone cement reinforced with calcium silicate fibers", J. Mater Sci: Mater Med (2014) 25:2357-2363.
NPL search for "phosphoserine" in PubChem; downloaded May 1, 2020.
Office Action issued for CN 201780059294.7 dated Apr. 6, 2021 (w/English translation) 21 pgs.
Office Action issued for U.S. Appl. No. 16/337,355 dated May 26, 2022, 8 pages.

(Continued)

*Primary Examiner* — Jeffrey T. Palenik
(74) *Attorney, Agent, or Firm* — Quarles & Brady LLP

(57) ABSTRACT

The present invention relates to a soft tissue adhesive comprising an aqueous composition comprising α-TCP and a phosphorylated amino acid. The composition has improved mechanical strength and is easily applied to the tissue.

11 Claims, 7 Drawing Sheets

(56) References Cited

OTHER PUBLICATIONS

Office Action issued for U.S. Appl. No. 16/337,355 dated Aug. 2, 2022, 18 pages.

Office Action issued for U.S. Appl. No. 16/337,355 dated Jan. 5, 2023, 13 pages.

Office Action issued for U.S. Appl. No. 16/337,355 dated Aug. 1, 2023, 18 pages.

Office Action issued for U.S. Appl. No. 16/337,355 dated Mar. 12, 2024, 15 pages.

Schneiders et al., "Effect of modification of hydroxyapatite/collagen composites with sodium citrate, phosphoserine, phosphoserine/RGD-peptide and calcium carbonate on bone remodeling", Bone 40 (2007): 1048-1059.

van Loghem J, et al., "Managing intravascular complications following treatment with calcium hydroxylapatite: An expert consensus" J Cosmet Dermatol. 2020;19(11):2845-2858. doi:10.1111/jocd.13353.

Fig. 1

| Material | Bonded to skin (Peak strength) |
|---|---|
| Cancellous | 13.9 |
| Cortical | 7.2 |
| Cartilage | 3.86 |
| Stainless steal | 2.54 |
| Aluminum | 2.44 |
| Copper | 4.33 |
| Teflon | 2.88 |

Fig. 7

SOFT TISSUE ADHESIVE COMPOSITION OF ALPHA-TCP AND PHOSPHORYLATED AMINO ACID

CROSS-REFERENCE TO RELATED APPLICATIONS

This application is a Continuation of U.S. application Ser. No. 16/337,350, entitled "SOFT TISSUE ADHESIVE COMPOSITION OF ALPHA-TCP AND PHOSPHORYLATED AMINO ACID", filed on Mar. 27, 2019, which application claims priority to and is a 35 U.S.C. § 371 national phase application of PCT/EP2017/074553 (WO2018/060289), filed on Sep. 27, 2017, entitled "SOFT TISSUE ADHESIVE COMPOSITION OF ALPHA-TCP AND PHOSPHORYLATED AMINO ACID", which application claims priority to and the benefit of Sweden Patent Application No. 1651271-7, filed Sep. 27, 2016 and Sweden Patent Application No. 1651727-8, filed Dec. 22, 2016, the disclosures of which are incorporated herein by reference in their entirety. Any disclaimer that may have occurred during the prosecution of the above-referenced applications is hereby expressly rescinded, and reconsideration of all relevant art is respectfully requested.

FIELD OF THE INVENTION

The present invention relates to a soft tissue adhesive of an aqueous solution of α-TCP and a phosphorylated amino acid. The invention further relates to a method of treating tissue.

BACKGROUND

Calcium phosphate (CaP) and in particular hydroxyapatite ($Ca_{10}(PO_4)_6(OH)_2$, HA), is a mineral that is widely used in medical applications due to its similarity to the mineral components of bone and teeth and its biocompatibility. Furthermore hydroxyapatite is non-toxic, biocompatible and bioactive. This means that hydroxyapatite is not harmful and not recognized as a foreign body and on the other hand that it may have positive effects on remodelling of bone. Hence hydroxyapatite has been widely used in bone repair and as drug/gene delivery vehicle, catalyst, ion adsorption/exchange agent, photoelectric regent and so on. Resorbable nanoparticles (i.e. particles that can be dissolved in vivo) are of special interest for a number of applications, e.g. bone void fillers, drug delivery vehicle, desensitization of dentin tubuli and so on.

The field of biomaterials includes fixation of implants to tissues as well as tissue repair. The limited mechanical strength of implants in combination adhesives has remained an issue within the field of implants and biomaterials. The repair of soft tissues or internal organs with adhesives has also been broadly unsuccessful.

US2012288446 (US'446) discloses an adhesive comprising a multivalent metal compound, a compound comprising a phosphoserine oligomer or a phosphoserine capped polymer wherein the latter compound is present at 10-90 wt %. US'446 discloses experimental data using tetra calcium phosphate (TTCP) as the multivalent metal compound and phosphoserine-ethyleneglycol-diglycidyl-phosphoserine for example and obtains adhesive strength of up to 3.76 MPa when adhered to bone.

US20130122057 (US'057) discloses a bone restorative composition comprising amino acid phosphate species, a multivalent metal compound and a bioactive glass material containing ionic functional groups. US'057 disclose examples using a composing comprising TTCP as the multivalent metal compound and phosphoserine together with various amounts of Combeite Bioactive glass and water and adhere it to bone. The shear strengths obtained varied between 0.75-2.13 MPa.

US8765189 (US'189) teaches an adhesive composition comprising a multivalent metal compound and a phosphoserine like compound in an amount of 10-90 wt %. US'189 disclose an adhesion shear strength to cortical bone after 5 minutes of 130-890 kPa when using TTCP as the multivalent metal compound and various phosphorylated compounds and 650 kPa when using α-TCP and phosphoserine.

Even though there are several tissue adhesives available today on the market none of them are ideal sealants or even adhesives. Cyanoacrylates have shown good adhesion but have shown inflammatory response during degradation. Fibrin glues have low adhesive strength but are more biocompatible. Other adhesives struggle with high costs and long curing times or the lack of tailoring the curing time dependent on the tissue and the situation. Soft tissue adhesive usually contain fibrin or gelatin other various polysaccharides.

Still general tissue adhesives cannot withstand any major shear forces and none of them have shown or implied that they would work also on soft tissues. There is therefore a need for a composition that may be used as a soft tissue adhesive that provides high shear strength.

SUMMARY OF THE INVENTION

The aim of the present invention is to overcome the drawbacks of the prior art. Therefore, in a first aspect, the present invention relates to a soft tissue adhesive comprising an aqueous solution, α-TCP and a phosphorylated amino acid. The adhesive effect of the present invention on soft tissue was unexpected since the composition contains α-TCP which is typically used in hard tissue applications.

In a second aspect the present invention relates to a method of adhering a first soft tissue to a second soft tissue using the tissue adhesive according to the present invention comprising:

a. applying the tissue adhesive according to the present invention to the first soft tissue or to the second soft tissue and optionally leave it for a suitable period of time;
b. bringing the first soft tissue and the second soft tissue into contact with each other;
c. optionally applying a pressure on the first and second soft tissue for a suitable period of time; and
d. allowing the tissue adhesive to cure.

In a third aspect the present invention relates to the use of a composition comprising an aqueous solution, α-TCP and a phosphorylated amino acid as a soft tissue adhesive.

In a fourth aspect the present invention relates to the use of a kit for preparing the adhesive according to any one of claims 1 to 10 comprising at least two containers wherein any one container in the kit can contain any of an aqueous solution, the phosphorylated amino acid or the α-TCP or a combination thereof, with the proviso that both the phosphorylated amino acid and the α-TCP cannot be present in the same container as the aqueous solution.

In a fifth aspect the present invention relates to a composition for use as a soft tissue adhesive comprising an aqueous solution, α-TCP and a phosphorylated amino acid.

All the embodiments presented herein relates to all the aspects of the present invention.

BRIEF DESCRIPTION OF THE FIGURES

FIG. 1 Rendering of different chemical interactions, bonding, and structure of a composition including calcium phosphate, water and phosphoserine.

FIG. 7 Bond strength of soft tissue to different substrates.

DETAILED DESCRIPTION OF THE INVENTION

Figure 2:
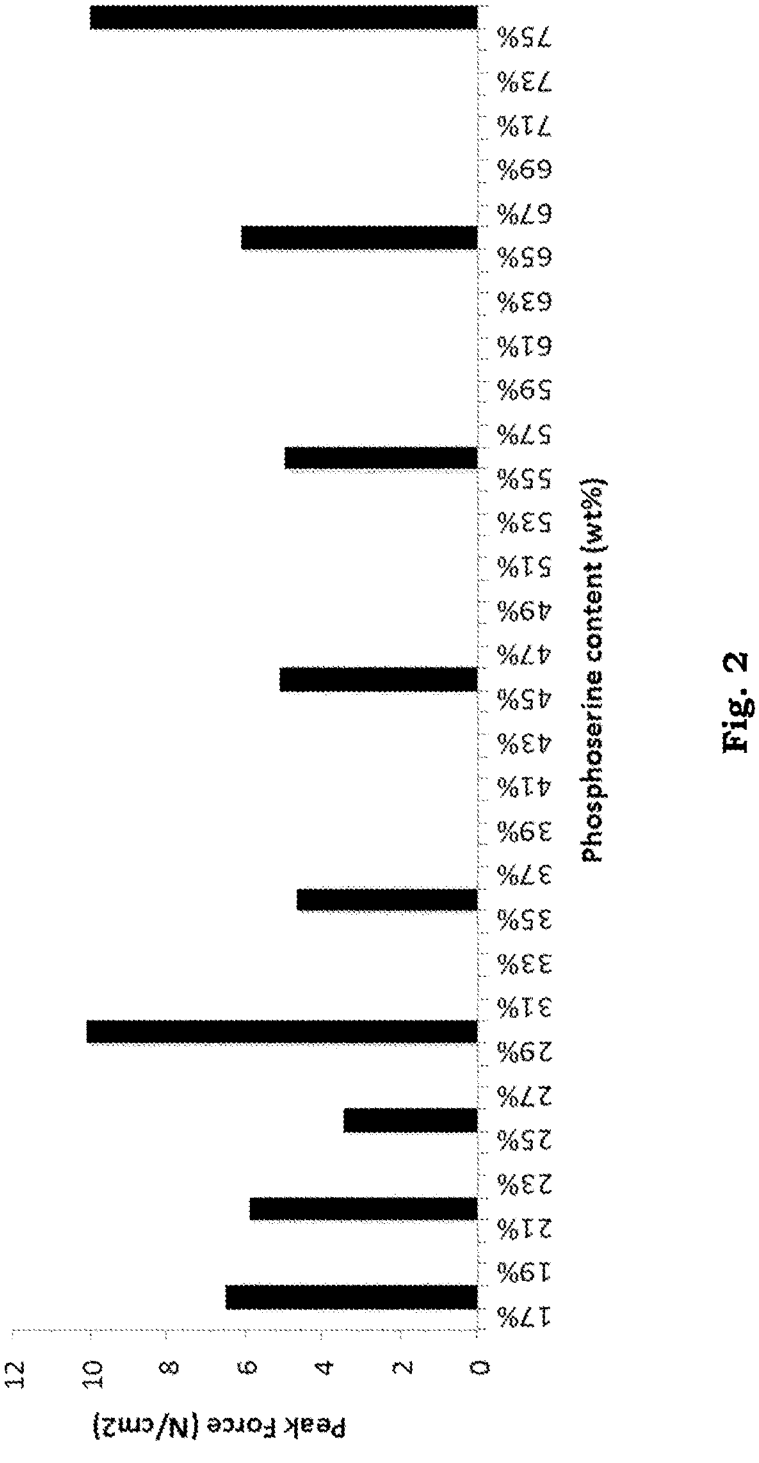
FIG. 2 Porcine skin lap shear after curing for 1.5 hours.

In the present application the word "aqueous solution" also encompasses water and water of any purity. The water may be but is not limited to tap water, distilled water or deionized water. The aqueous solution may also be a buffer such as PBS or any suitable saline buffer.

The Composition

The composition according to the present invention is an aqueous composition comprising α-TCP and a phosphorylated amino acid.

The present inventors have found that this composition provides improved mechanical strength and easy handling when treating soft tissue. Also the composition has shown to be suitable for adhering soft tissue to either hard tissue or a synthetic implant or scaffold but also soft tissue to soft tissue. The latter is a long felt need within the field and the present invention not only facilitates adherence of soft tissue to soft tissue but the mechanical strength of the adhesive is unexpectedly high and the curing is fast.

Surprisingly the present inventors found that the improvements of the present composition were only true for α-TCP but not for β-TCP. The α-TCP may be used in any form or shape but is preferably in form of a powder having a mean particle size of 5-5000 nm such as 20 nm or larger, 50 nm or larger, 100 nm or larger, or 300 nm or larger, or 500 nm or larger, or 800 nm or larger, or 3000 nm or smaller, or 1500 nm or smaller, or 1000 nm or smaller. In one embodiment the particle size is between 350 and 450 nm. In another embodiment the particle size is between 1700 nm and 2800 nm. The particles may be spherical or in the shape of flakes.

The composition may comprise a silicate compound. In one embodiment the composition is essentially free from silicate compounds or totally free from silicate compounds. In another embodiment the amount of silicate compounds is 0.05 wt % to 10 wt % of the solid content of the composition such as 0.1 wt % or higher, or 0.5 wt % or higher, or 8 wt % or less, or 5 wt % or less, or 3 wt % or less, or 1 wt % or less.

The silicate compound may be any suitable compound comprising a silicate i.e. an anionic silicon compound. The silicon compound may be an oxide such as $[SiO_4]^{2-}$ or $[Si_2O_7]^{6-}$ or quartz, feldspars, zeolites, micas, pyroxene etc. In one embodiment the silicate compound is selected from calcium silicate, sodium silicate and aluminum silicate, magnesium silicate, strontium silicate; zirconium silicate; or a mixture of di- and tri-calcium silicate preferably calcium silicate. The silicates may be in the form of a cement such as Portland grey cement or Portland white cement. A mixture of di- and tricalcium silicate may comprise between 0-100 wt % of dicalcium silicate and between 0-100 wt % of tricalcium silicate such as 30-70 wt % of di-calcium silicate and 30-70 wt % of tri-calcium silicate.

Phosphorylation is the addition of a phosphate group ($PO_4^{3-}$) to an amino acid or any other molecule. Phosphorylated amino acids according to the present invention may for example be phosphorylated serine, threonine or tyrosine but could also be other amino acids. In one embodiment the phosphorylated amino acid is phosphorylated serine also known as phosphoserine (pSer). The phosphorylated amino acids according to the present invention may be functionalized or non-functionalized. The phosphorylated amino acids according to the present invention may be monomers or dimers or trimers.

It is believed that the phosphorylated amino acid acts as a curing agent providing improved mechanical strength to the composition. The amount of phosphorylated amino acid should be 15-90 wt % of the solid content of the composition. In order to balance the different properties of the inherent components of the composition the amount of phosphorylated amino acid may depend on the ratio between the silicate compound and the α-TCP. In one embodiment a preferred amount of phosphorylated amino acid is 20-75 wt % of the solid content such as 22 wt % or more, or 25 wt % or more, or 30 wt % or more, or 35 wt % or more, or 65 wt % or less, or 60 wt % or less, or 55 wt % or less, 45 wt % or less, or 40 wt % or less, or 36 wt % or less. In one embodiment the amount of phosphorylated amino acid is 23-24 wt % of the solid content of the composition. In another embodiment the amount of phosphorylated amino acid is 69-74 wt %.

For soft tissue-to-soft tissue adhesion in dry to humid conditions, the amount of phosphorylated amino acid in the solid content of the composition may be high, for example 40-90 wt %, 43-90 wt %, 45-90 wt %, 50-90 wt %, 55-90 wt %, 60-90 wt %, 65-90 wt %, 70-90 wt %, 75-90 wt %, 80-90 wt %, or 60-80 wt %, 60-70 wt %, 65-80 wt %, and 70-80 wt %. A high phosphorylated amino acid content generates a softer modulus which is beneficial for soft tissue adhesion.

For wet and humid to dry environment, the amount of phosphorylated amino acid in the solid content of the composition should be lower to avoid a washing-away effect. The amount of phosphorylated amino acid in the solid content of the composition may for example be 15-37 wt %, 15-35 wt %, 15-33 wt %, 15-31 wt %, 15-29 wt %, 15-27 wt %, and 15-25 wt %.

For the composition comprising α-TCP and a phosphorylated amino acid for use as a soft tissue adhesive the amount of α-TCP may be 50 wt % or higher, or 60 wt % or higher, or 70 wt % or higher but 90 wt % or lower, or 85 wt % or lower, or 80 wt % or lower of the solid content. In one embodiment at least 95 wt % of the composition comprises an aqueous solution, α-TCP and a phosphorylated amino acid, such as at least 98 wt %, or at least 99 wt %. In one embodiment the composition comprising an aqueous solution, α-TCP and a phosphorylated amino acid for use as a soft tissue adhesive does not comprise any silicate compound.

As to alternative constituents, calcium oxide (CaO) should be avoided in larger amounts. Firstly, it is very reactive, and produces heat (exothermic), which forcefully accelerates the reaction. There are also 2-3 different types of calcium oxide, with the OH and OH2 forms being less reactive. Additionally, it is notoriously difficult to maintain the oxide in a constant state, it converts to more hydrated forms. There may be some benefits when it comes to handling, since it readily absorbs water, but generally it will give negative effects. In one embodiment, the CaO may be present in concentrations below 5 wt %, preferably below 3 wt %, even more preferably below 1 wt %, and most preferably CaO is only present between 0 wt % and trace amounts. The use of a phosphorylated amino acid can replace the need for CaO and improve the properties of the soft tissue adhesive.

The composition may comprise any suitable amount of aqueous solution for example 5-95 wt % of the total weight of the composition, such as 10 wt % or more, or 15 wt % or more, or 20 wt % or more, or, or 90 wt % or less, or 80 wt % or less, or 70 wt % or less, or 60 wt % or less, or 50 wt % or less, or 40 wt % or less, or 30 wt % or less, or 25 wt % or less. Increasing amount of water reduces the strength of bonding. The water may be distilled or deionized water or any water of high purity but tap water may also be used. The aqueous solution may also be in the form of a hydrogel such as hyaluronic acid, polyvinyl alcohol, chitosan, collagen or a combination thereof. By using a hydrogel as the aqueous solution the composition may more easily remain at the wanted location during curing.

An advantage of the present invention is that the curing time may be tailored so that it cures at the right moment. This is dependent on the application. Sometimes the composition should cure very rapidly and sometimes the composition should be mixed or shaped for a while and when applied it might need some adjustment and therefore the curing should be postponed.

A retardant such as sodium citrate may be added to the reaction mixture and the amount may be 0.1-40 wt % (solid content) or 0.8-8 wt % of the total weight of the composition. In one embodiment the amount of the retardant is 3.5-7 wt % of the solid content. The retardant may be but is not limited to sodium citrate or citric acid. The composition may further comprise additives such as growth factors, nutrients, anti-oxidants and so on. But the composition works without retardants and additives and in one embodiment at least 95 wt % of the solid content of the composition comprises α-TCP, phosphorylated amino acid and silicate compound, such as at least 98 wt %, or at least 99 wt %.

Preparing and Curing of the Composition

The composition is formed by mixing the solid components α-TCP and phosphorylated amino acid with the aqueous solution.

Preparing the composition may be done by premixing the silicate, phosphoserine (pSer) and α-TCP powders. The mixing may be done by stirring, kneading or shaking using any suitable means. The aqueous solution is then added and mixed. Formulations with higher amounts of pSer are easy to mix, while some formulations require mechanical force to obtain a good mixture. The mixing is done during a couple of seconds such as 10-30 seconds and may then be allowed to set for a couple of seconds, 5-120 seconds, prior application. The phosphorylated amino acid may be pre-dissolved in a solvent before adding the α-TCP.

The curing may be done at any suitable temperature. In one embodiment the mixing is done at room temperature or below, 10-25° C., and kept at 25° C. or lower, such as 10-20° C. After applying the composition the curing temperature is preferably increased to 37° C. or higher.

Curing of the composition will occur when mixing the solid components α-TCP and phosphorylated amino acid with the aqueous solution. The curing reaction will lead to the formation of a thick paste and ultimately a solid cement.

The composition according to the present invention may have a shear strength to skin of at least 10 kPa, or at least 25 kPa, or at least 50 kPa, or at least 75 kPa when measured after 1.5 h of curing at 100% humidity and 37° C.

The composition according to the present invention may have a shear strength to tendon of at least 25 kPa, or at least 50 kPa, or at least 75 kPa when measured after 1.5 h of curing at 100% humidity and 37° C.

The composition according to the present invention may have a shear strength to collagen of at least 15 kPa, or at least 19 kPa when measured after 1.5 h of curing at 100% humidity and 37° C.

Applications

The composition according to the present invention may be used for a variety of applications. Due to the ease of applying the composition and the mechanical strength of the cured composition the composition may be used as an adhesive for biological tissue. By applying the composition to soft tissue another soft tissue or the same soft tissue may be adhered and a sufficient mechanical strength is formed between the two soft tissues. The soft tissue may be selected from but is not limited to tendon, ligament, cartilage, fascia, skin, fibrous tissue, muscle, fat, nerve, blood vessel, liver, stomach, hair, nails, eye lashes, intestines, bladder, brain, eyes, uterus, lungs, esophagus, heart, lung, kidney, spleen and glands. In one embodiment the soft tissue is selected from fascia, skin, fibrous tissue, muscle, fat, nerve, blood vessel, liver, stomach, intestines, bladder, brain, eyes, uterus, lungs, esophagus, heart, lung, kidney, spleen and glands. In one embodiment the soft tissue is cartilage or tendon. In one embodiment the soft tissue adhesive according to the present invention is used to adhere a soft tissue to a hard tissue, or adhere two different soft tissues together. In one embodiment the soft tissue is a tissue having an extra cellular matrix, collagen and elastin. In another embodiment the soft tissue is a tissue having an epithelium. FIGS. 4 to 8 disclose the peak force when the present composition is used for different tissues.

An implant or a scaffold may also be adhered to a soft tissue by using the composition according to the present invention. The implant or scaffold may be made of synthetic or biological material or a combination thereof. Synthetic materials may be metal, polymers or ceramics where the metals may be titanium, niobium or alloys of the same or aluminum oxide, stainless steel, where the polymers may be polyurethane, polyesters (e.g. polylactic acid, polyglycolic acid, polycaprolactone), polyacrylates (e.g. polymethyl methacrylate, poly(2-hydroxyethyl methacrylate)), polyethers (e.g. polyethylene glycol), polysiloxanes (eg. Silicone), hydrogels (e.g. polyvinyl alcohol) and polyvinyls (e.g. polyethylene, polypropylene, polyisbutylene, polystyrene) and where the ceramics may be calcium phosphates (e.g. hydroxyapatite, monetite, tetra calcium phosphate), metal oxides (e.g. aluminum oxides, zirconium oxides, titanium oxides) or bioglass. The implant may be an car, fixation material, screw or tubes. Biological materials may be, but are not limited to, collagen, hyaluronic acid, chitosan, cells, tissue, decellularized tissue, platelet rich plasma, Matrigel®, demineralized bone, fibrin, cellulose, synthetic or natural silk etc. The material may be in the shape of particles, fibres or a solid surface.

During the healing process after treating damaged tissue the tissue or the scar lacks the sufficient mechanical strength and the repaired tissue may leak body fluids. The present invention may be used to further strengthen the tissue during healing or scar formation and may even be used to seal the tissue in order to minimize leakage of body fluids. For example in combination with sutures the present composition may be added to the tissue section to be sutured together in order to provide further strength and scaling.

Figure 5:
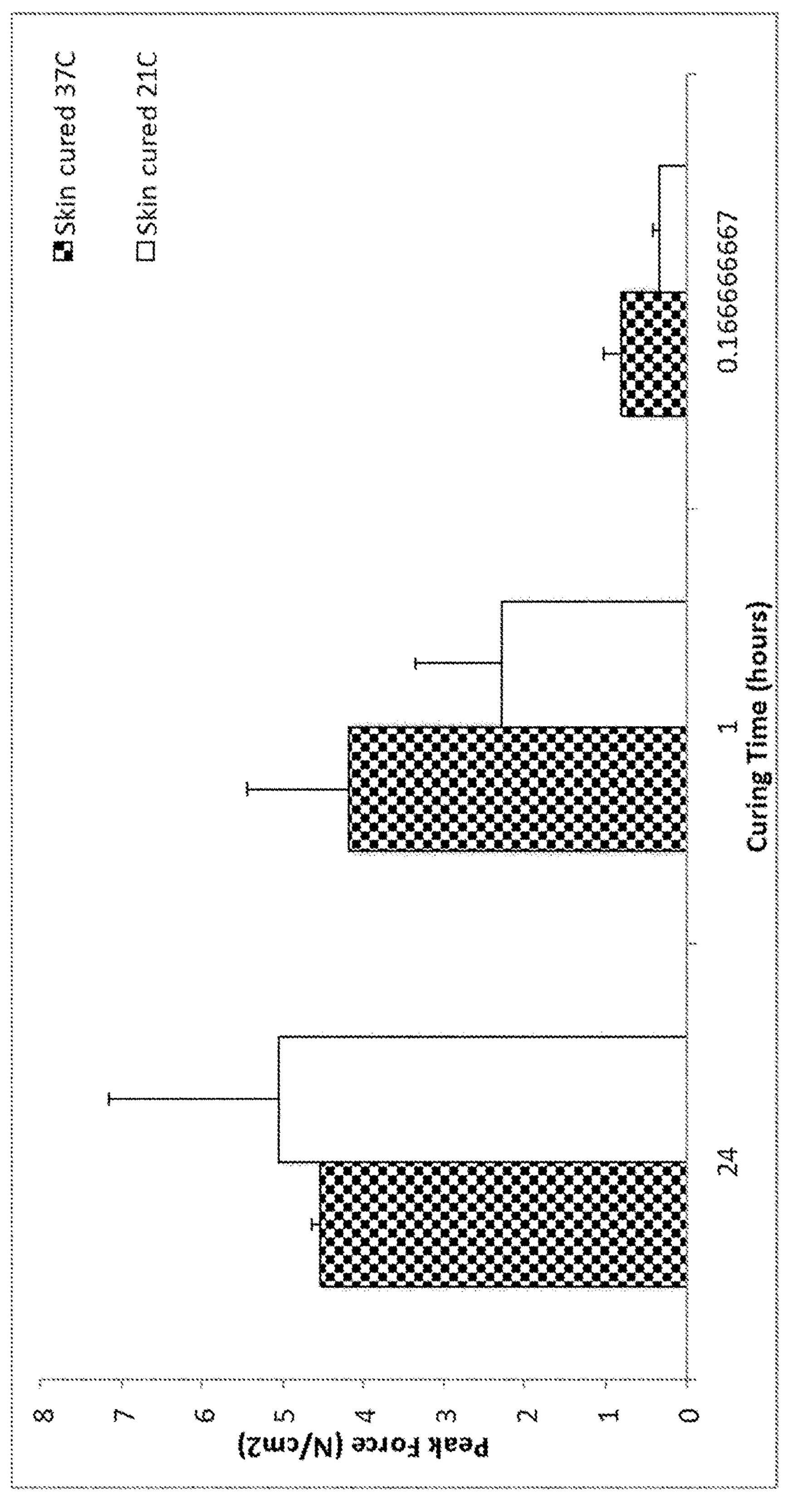
FIG. 5 Porcine skin lap shear strength development with varied curing temperatures.

Adhering of a first tissue to a second surface may be done by applying the tissue adhesive or the composition according to the present invention to the first tissue. This may for example be two or more tissues or a tissue to a surface such as an implant or scaffold. The composition may also be applied to the second surface as well. The adhesive may be left for a suitable period of time before bringing the two or more tissues or surfaces into contact with each other. The time is dependent on content of the adhesive and the curing time and also on the tissues or materials but non-limiting examples are 10 seconds or longer, or 30 seconds or longer, or 1 minute or longer, or 5 minutes or longer. In one embodiment the composition is left for 20 seconds to 60 seconds before bring the two or more tissues or surface into contact with each other. The surfaces are then brought into contact with each other and if necessary pressure may be applied. The pressure is applied depending on the tissue/material and the cure time of the composition but non-limiting examples are 10 seconds or longer, or 30 seconds or longer, or 1 minute or longer, or 5 minutes or longer. In one embodiment a pressure is applied for 1-3 minutes. In order to cure the composition faster energy may be applied to the composition or to the part of the tissue to which the composition have been applied. This may be done by applying UV, heat or radiation of any suitable type for a couple of seconds up to minutes. The adhesive or the composition is then left to cure to the final cured composition. The adhesive may be fully cured after 5 minutes up to 48 hours depending on the composition and the tissue or surface. FIG. 5 shows the peak force (maximum force before breaking) after different curing times.

The curing time is dependent on the ratios of the inherent components however due to that the composition starts to cure when mixed the composition is mixed together at a suitable time prior to use or application. In certain applications the composition should cure rapidly after application of the composition and in other applications a slower curing is wanted. The present invention facilitates tailoring of the curing time so that the user may prepare the composition on beforehand without having a fully cured composition when it is time to apply it or prepare it to obtain a composition that is still shapeable or to prepare a composition that cures almost instantly.

The method may be performed in vivo or in vitro but some of the steps may be done in vitro followed by steps done in vivo. Injuries that require replacement of large pieces of tissue are unable to heal without intervention. Large pieces of tissue cannot currently be grown for implantation because oxygen and nutrients cannot penetrate deeper than 500 um-2 mm. One example of a solution to this problem is to grow multiple smaller pieces of tissue and to adhere them together (in vitro or ex vivo), immediately prior to implantation in vivo by using the composition according to the present invention.

The working time can be broken into three phases: The mixing and tacky phase, the dough phase and the final cured phase. During the mixing and tacky phase the mixture is casily mixed and flows with minor resistance. The preferred application period is near the end of the tacky phase and beginning of the dough phase. The dough phase is characterized by an increase in cohesion and decrease in adhesion. During the dough phase adhered tissue can be easily rearranged, aligned or even separated and reattached with minor effect on the final bond strength. However, during the dough phase application of the thickened and more cohesive mixture can be more difficult, thus the tacky phase is the preferred application period, while the dough phase is the preferred time for rearrangement. Finally, during the final cure phase the adhesive no longer moves easily, if at all, and revisions may significantly affect final bond strength.

Kit for Preparing the Composition

A kit comprising the different components of the composition may be used to prepare the present composition. The kit may comprise at least two containers where the containers may be any suitable type of container such as a bowl, bag, dish, plate, beaker, flask, tin, cup or bottle and may be of any size and shape. Any one container in the kit can contain any of an aqueous solution, the phosphorylated amino acid or the α-TCP or a combination thereof, with the proviso that both the phosphorylated amino acid and the α-TCP cannot be present in the same container as the aqueous solution. In other words one container may comprise the aqueous solution while a second or additional container may comprise the solid components (the phosphorylated amino acid and the α-TCP), or one container may comprise the aqueous solution and one of the solid components and the second container comprises the other two solid components, or one container comprises the aqueous solution and one of the solid components and the second container comprises the aqueous solution and the other two components (with the proviso that the other two components are not α-TCP and the phosphorylated amino acid). If a silicate compound is used it may be in the form of two or more reactants that may react to form the silicate compound. The two or more reactants may be in the same compartment or may be in separate compartments. In one embodiment the kit comprises three or more containers. The amount of aqueous solution, phosphorylated amino acid, silicate compound and α-TCP in the containers is such that when mixed the composition according to the present invention.

The kit may also be in form of a syringe having at least two compartments. The compartments in the syringe can contain any of an aqueous solution, the phosphorylated amino acid or the α-TCP or a combination thereof. However both the phosphorylated amino acid and the α-TCP cannot be present in the same compartment as the aqueous solution. In other words one compartment may comprise the aqueous solution while a second or additional compartment may comprise the solid components (the phosphorylated amino acid, the silicate compound and the α-TCP), or one compartment may comprise the aqueous solution and one of the solid components and the second compartment comprises the other two solid components, or one compartment comprises the aqueous solution and one of the solid components and the second compartment comprises the aqueous solution and the other two components (with the proviso that the other two components are not the α-TCP and the phosphorylated amino acid). If a silicate compound is used it may be in the form of two or more reactants that may react to form the silicate compound. The two or more reactants may be in the same compartment or may be in separate compartments. In one embodiment the kit comprises three or more compartments. The amount of water, phosphorylated amino acid, silicate compound and α-TCP in the compartments is such that when mixed the composition according to the present invention.

The syringe further comprises a mixing device that is configured to mix the components of the compartments during application of the components. The mixing device may be arranged at the tip of the syringe or within the compartments.

EXAMPLES

Example 1

Figure 1:
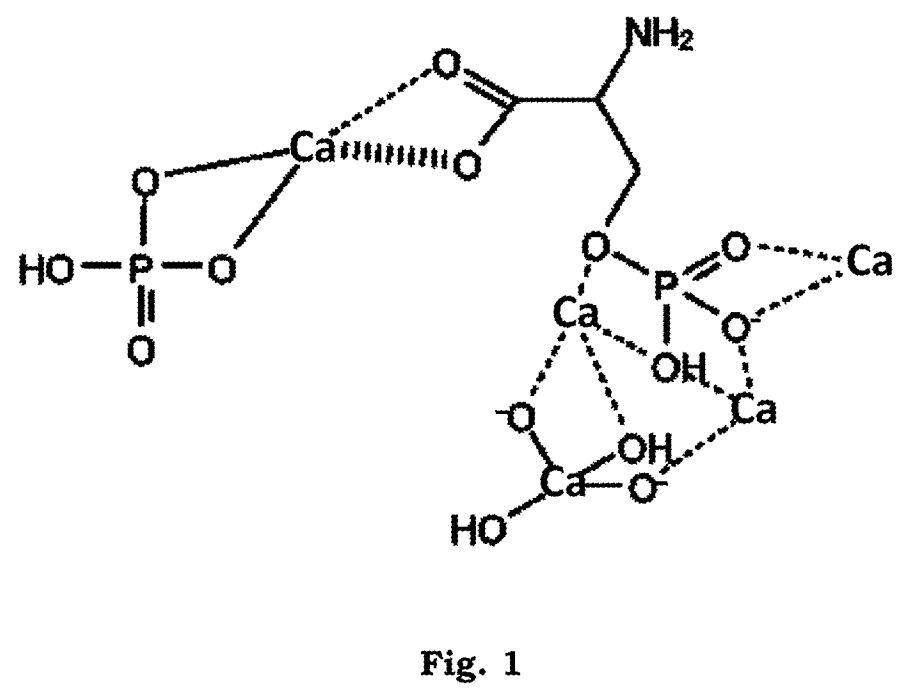

FIG. 1 discloses a schematic figure representing the bonding and structure of the set product.

Example 2

Fresh porcine skin, from the ear, was kept frozen (−20 C) and thawed at room temperature (21 C) for 3 hours prior to testing. Test size per sample was 0.256 g of powder and 53.3 uL of liquid. Skin was sectioned into strips 1.5 cm wide by 3 cm long, with an overlap of 1 cm. An adhesive formulation that included alpha-TCP and phosphoserine was applied to the overlap area, within 45-60 seconds of mixing, and then samples clamped together to ensure a complete sealing, then were sealed in a humid container and allowed to cure for 90 minutes. The X-axis represents the weight percentage comprised of phosphoserine, the Y-axis represents the peak force before failure occurred (N/cm$^2$). Lap shear testing was performing by fixing each end of the tissue (clamps) and applying tensile stress (pulling) at a speed of 5 mm/minute. Results are seen in FIG. 2.

Example 3

Fresh porcine skin, from the ear, was kept frozen (−20 C) and thawed at room temperature (21 C) for 3 hours prior to testing. Test size per sample was 0.256 g of powder and 53.3 uL of liquid. Skin was sectioned into strips 1.5 cm wide by 3 cm long, with an overlap of 1 cm. An adhesive formulation that included alpha-TCP and phosphoserine was applied to the overlap area, within 45-60 seconds of mixing, and then samples clamped together to ensure a complete sealing, then were sealed in a humid container and allowed to cure for 90 minutes. The results are disclosed in FIG. 3, the X-axis represents the curing time (in hours), the Y-axis represents the peak force before failure occurred (N/cm$^2$). Lap shear testing was performing by fixing each end of the tissue (clamps) and applying tensile stress (pulling) at a speed of 5 mm/minute.

Example 4

Figure 4:
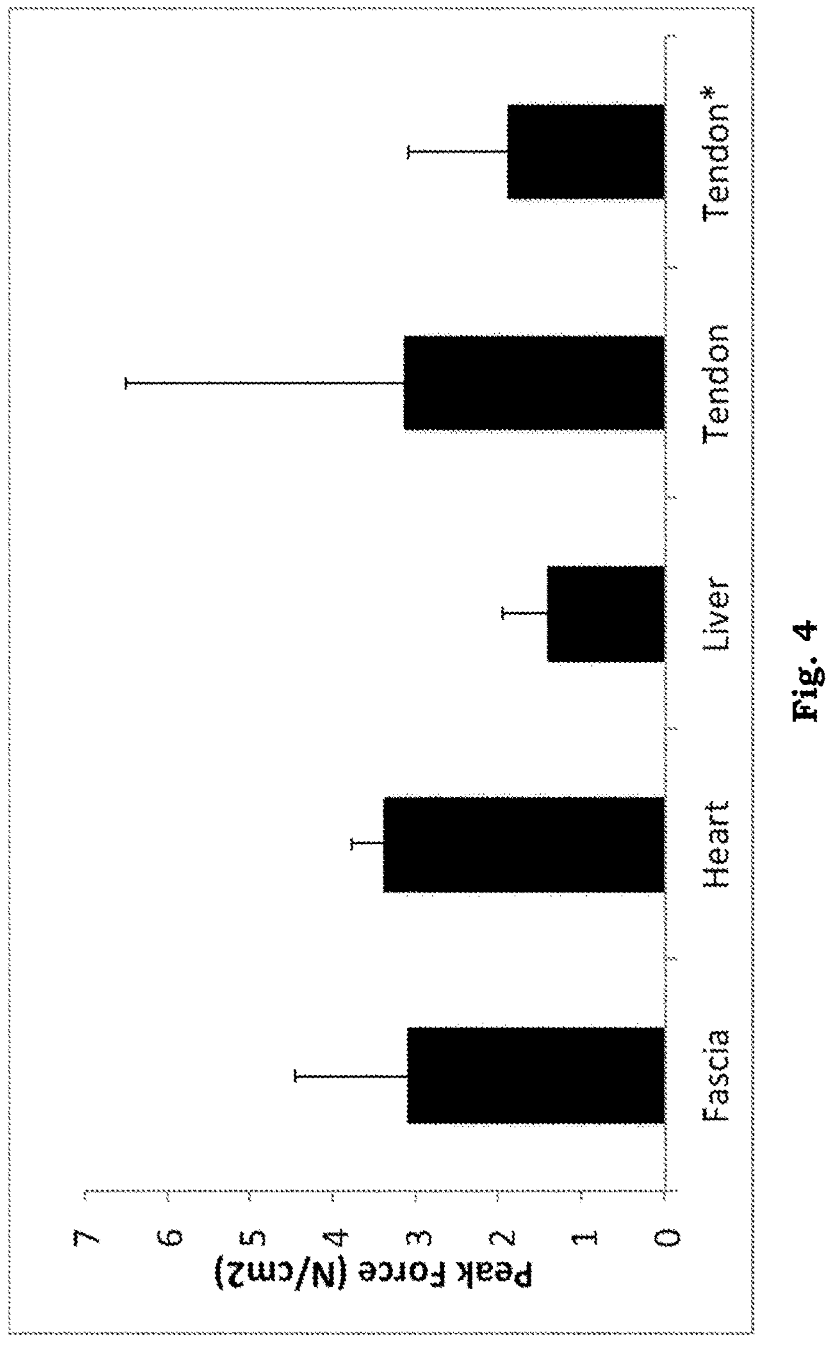
FIG. 4 Lap shear strength (peak force) of soft tissues adhered to self-tissue type.

As described in Example 2 and FIG. 2. An adhesive formulation that included alpha-TCP and phosphoserine was applied to the overlap area, within 45-60 seconds of mixing. The X-axis represents the different tissues adhered to self-tissue type. The Y-axis represents the average peak failure strength in newtons per centimeter squared (N/cm$^2$). Lap shear testing was performing by fixing each end of the tissue (clamps) and applying tensile stress (pulling) at a speed of 5 mm/minute. Values represent the peak force before failure occurred (N/cm$^2$). The sample labeled "Tendon" tested the lap shear strength of adhered overlapping tendon segments, while the sample labeled "Tendon*" represent the average value of tendons that were adhered at the severed faces on each end (end to end). Results are seen in FIG. 4.

Example 5

Figure 3:
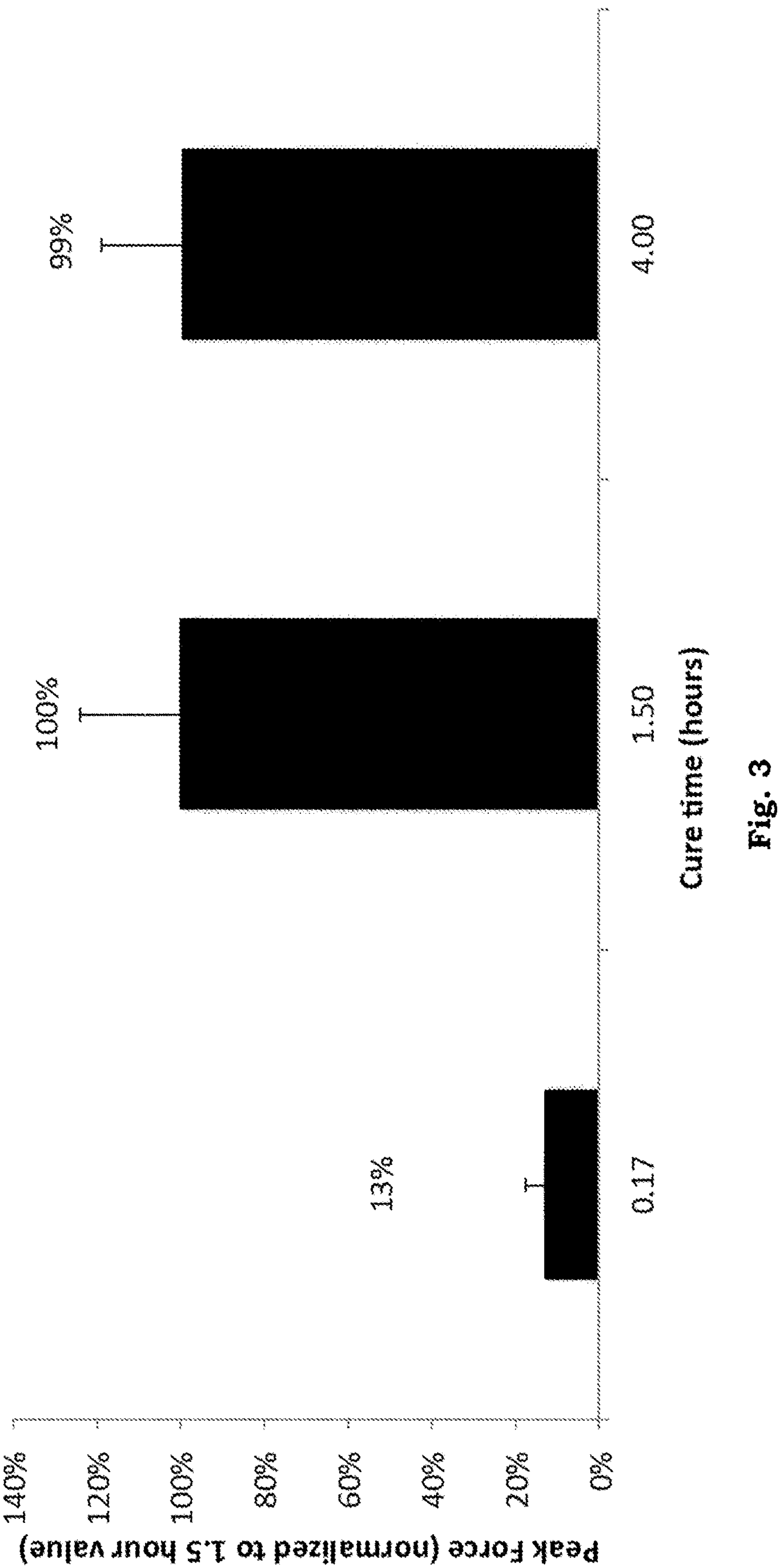
FIG. 3 Porcine skin lap shear strength after curing for 10 minutes (0.17 hours), 1.5 or 4 hours.

As described in Example 3 and FIG. 3, at different curing temperatures. Porcine skin strips were attached to self-tissue type (skin), with an approximate 1 cm overlap, and allowed to cure for 10 minutes, 1 or 24 hours. An adhesive formulation that included alpha-TCP and phosphoserine was applied to the overlap area, within 45-60 seconds of mixing, The X-axis represents the curing time, in hours. The Y-axis represents the average peak lap shear failure strength in newtons per centimeter squared (N/cm$^2$). Values represent the peak force before failure occured (N/cm$^2$). Results are seen in FIG. 5.

Example 6

Figure 6:
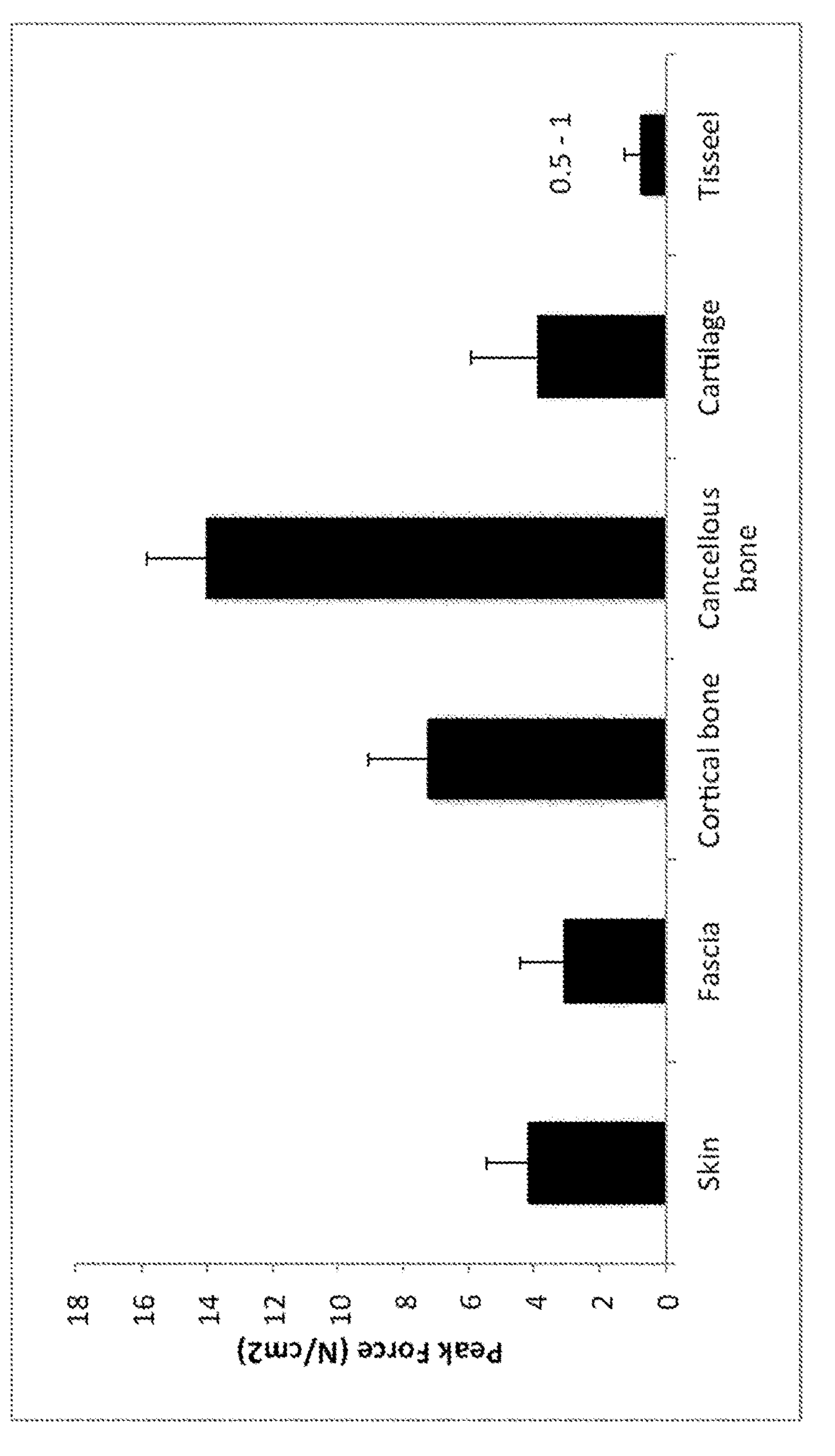
FIG. 6 Lap shear strength of soft tissue adhered to multiple tissue types.

As described in Example 2 and FIG. 2. Porcine skin strips were attached to hard and soft tissues, with an approximate 1 cm overlap, and allowed to cure for 1 hour, at 37 C in a humid environment. The values for Tisseel are taken from reported values in the scientific literature, and included for comparison only. The adhesive formulation including alpha-TCP and phosphoserine was applied to the overlap area, within 45-60 seconds of mixing, The X-axis represents the tissue type adhered to porcine skin. The Y-axis represents the average peak lap shear failure strength in newtons per centimeter squared (N/cm$^2$). Results are seen in FIG. 6.

Example 7

As described in above. Porcine skin strips were attached to hard and soft tissues, and materials associated with biomaterials or industrial materials. Skin was attached with an approximate 1 cm overlap, and allowed to cure for 1 hour, at 37 C in a humid environment. The adhesive formulation including alpha-TCP and phosphoserine was applied to the overlap area, within 45-60 seconds of mixing, The X-axis represents the tissue or material type adhered to porcine skin. The Y-axis represents the peak lap shear failure strength in newtons per centimeter squared (N/cm$^2$). Results are seen in FIG. 7.

The invention claimed is:

1. A method of adhering a first soft tissue to a second soft tissue using a tissue adhesive comprising an aqueous solution, α-TCP, and a phosphorylated amino acid, wherein the tissue adhesive does not comprise a silicate compound, wherein the method comprises:

a. applying the tissue adhesive to the first soft tissue or to the second soft tissue and optionally leave it for a suitable period of time;

b. bringing the first tissue and the second tissue into contact with each other;

c. optionally applying a pressure on the first and second tissue for a suitable period of time; and d. letting the tissue adhesive cure;

wherein the amount of phosphorylated amino acid is 40-90 wt % of the solid content.

2. The method according to claim 1 wherein the steps are performed in vitro.

3. The method according to claim 1 wherein the amount of the phosphorylated amino acid is 60-80 wt %.

4. The method according to claim 1 wherein at least 95 wt % of the tissue adhesive comprises the aqueous solution, α-TCP and the phosphorylated amino acid.

5. The method according to claim 1 wherein at least 98 wt % of the tissue adhesive comprises the aqueous solution, α-TCP and the phosphorylated amino acid.

6. The method according to claim 1 wherein at least 98 wt % of the tissue adhesive comprises the aqueous solution, α-TCP and wherein the amount of phosphorylated amino acid is 60-80 wt %.

7. The method according to claim 1 wherein the phosphorylated amino acid is phosphorylated serine.

8. The method according to claim 1 wherein the aqueous solution is water.

9. The method according to claim 1 wherein the tissue adhesive further comprises a hydrogel.

10. The method according to claim 1 wherein the tissue adhesive further comprises collagen.

11. The method according to claim 1 wherein at least one of the first and the second soft tissue is selected from tendon, ligament, fascia, skin, fibrous tissue, muscle, fat, nerve or blood vessel.

* * * * *